United States Patent
Knox

[19]

[11] Patent Number: 6,052,058
[45] Date of Patent: Apr. 18, 2000

[54] FILTER INTEGRITY MONITORING SYSTEM

[75] Inventor: Ronald Knox, Mornington, Australia

[73] Assignee: Vision Products Pty. Ltd., Australia

[21] Appl. No.: 09/171,896

[22] PCT Filed: May 6, 1997

[86] PCT No.: PCT/AU97/00270

§ 371 Date: Oct. 28, 1998

§ 102(e) Date: Oct. 28, 1998

[87] PCT Pub. No.: WO97/42487

PCT Pub. Date: Nov. 13, 1997

[30] Foreign Application Priority Data

May 6, 1996 [AU] Australia ............... PN 9689

[51] Int. Cl.⁷ .................................................. G08B 21/00
[52] U.S. Cl. ................... 340/607; 340/608; 340/609; 340/610; 340/626; 340/628
[58] Field of Search ............................. 340/607, 608, 340/609, 610, 457, 626, 628, 457.4

[56] References Cited

U.S. PATENT DOCUMENTS

| | | |
|---|---|---|
| 4,389,903 | 6/1983 | Bertone et al. ...................... 73/863.03 |
| 5,053,754 | 10/1991 | Wong ....................................... 340/632 |
| 5,205,156 | 4/1993 | Asano et al. .................................. 73/38 |
| 5,381,130 | 1/1995 | Thuillard et al. ........................ 340/630 |
| 5,606,311 | 2/1997 | Polidan et al. ............................ 340/607 |
| 5,610,592 | 3/1997 | Okazaki ................................... 340/628 |
| 5,831,537 | 11/1998 | Marman .................................. 340/628 |

FOREIGN PATENT DOCUMENTS

| | | | |
|---|---|---|---|
| 0059593 A1 | 9/1982 | European Pat. Off. | ....... G01N 21/39 |
| 0119353 A2 | 9/1984 | European Pat. Off. | ....... G01N 21/53 |
| 0455125 A2 | 11/1991 | European Pat. Off. | ....... G01N 33/53 |
| 2051514 | 1/1981 | United Kingdom | ........... G01S 17/46 |
| 2267963 | 12/1993 | United Kingdom | ......... G08B 17/103 |

*Primary Examiner*—Daniel J. Wu
*Assistant Examiner*—Tai T. Nguyen
*Attorney, Agent, or Firm*—Wolf, Greenfield & Sacks, P.C.

[57] ABSTRACT

A method and system for monitoring integrity of a filter (25) of a smoke or fire detector system. The system has a detector chamber (14) into which light is passed from a light source incorporated into a light source control circuit (10). Scattered light is detected by a light scatter detector (12). Controller circuit (16) receives signal from the detector (12) and makes a cumulative count over time of the number of dust particles detected.

19 Claims, 6 Drawing Sheets

FILTER INTEGRITY MONITORING SYSTEM

FIELD OF THE INVENTION

This invention relates to a filter integrity monitoring system, for example for use with a smoke detection system of the kind a detector producing an electrical output which is a measure of the concentration, in the air, of particles indicative of the presence of smoke or fire.

BACKGROUND OF THE INVENTION

Fire protection and suppressant systems may operate by detecting the presence of smoke and other airborne pollutants. Upon a threshold level of smoke being detected, an alarm may be activated and operation of a fire suppressant system may be initiated. While the fire itself will cause damage, considerable damage can also be caused by operation of the fire suppression system and subsequent removal of the suppressant can be quite hazardous. Many traditional suppressants, such as halon, are also ozone depleting whereby this use is environmentally undesirable. A detection system which is sufficiently sensitive to detect an abnormal condition prior to the onset of a fire is very advantageous as it enables action to be taken at a very early stage before the onset of actual fire conditions. For example, when most substances are heated, even before heating occurs to a point at which a fire commences, emissions will be generated and if these can be detected by a very sensitive system, a warning provided at that very early stage may allow the problem to be detected and rectified, or the equipment turned off, before the fire actually starts.

The detection system may incorporate a sampling pipe network consisting of one or more sampling pipes with sampling holes installed at positions where smoke or pre-fire emissions can be collected. Air is drawn in through the sampling holes and along the pipe by means of an aspirator or fan and is directed through a detector at a remote location.

Although there are a number of different types of smoke detectors which can be used as the detector in a system as outlined above, one particularly suitable form of detector for use in such a system is an optical scatter detector which is able to provide good sensitivity at reasonable cost. Optical scatter detectors operate on the principle that smoke particles or other airborne pollutants of small size when introduced into a detection chamber and subjected to a high intensity light beam will cause light scatter. The scattered light is sensed by a scattered light detector. The greater the amount of smoke particles within the sample introduced into the detector chamber the greater will be the amount of light scatter. The scatter detector detects the amount of scattered light and hence is able to provide an output signal indicative of the amount of smoke particles or other pollutant particles within the sample flow.

A difficulty arises in operation of smoke detector systems of the above kind in that most atmospheres where smoke or fire detection is required contain dust which may interfere with operation of the system. A filter may therefore be incorporated into the system for the purpose of keeping dust away from sensitive optical surfaces and to prevent dust from artificially affecting the detection of particles or gasses which are indicative of presence of fire of smoke. For example with optical scatter type detectors, the presence of dust may seriously affect the detector output since dust particles are generally larger than the particles which are indicative of the presence of smoke or fire and produce more scattered light than those particles.

A difficulty with the use of filters is that the filter will eventually fill with dust which can prevent passage therethrough of particles the presence of which it is desired to detect, so that the effective sensitivity of the detector system drops.

SUMMARY OF THE INVENTION

In one aspect, the invention provides a method of producing an indication of blockage of a dust filter in a smoke or fire detection system of the kind having a detector for producing an output indicative of the level of emissions of the products of smoke or fire in air, and the filter being arranged to filter dust from said air before application to the detector, comprising detecting dust particles in said air either before or after passage through said filter and making a cumulative count over time of the number of so detected dust particles up to a terminal count at which time an indication is given that the filter is becoming blocked and should be replaced.

The invention also provides a filter blockage monitoring system for use with a smoke or fire detection system of the kind having a detector for producing an output indicative of the level of emissions of the products of smoke or fire in air, and a filter being arranged to filter dust from said air before application to the detector, said detector producing in said output an identifiable output in the event of detection of a dust particle, said filter blockage monitoring system comprising means for detecting dust particles in said air either before or after passage through said filter and making a cumulative count over time of the number of so detected dust particles up to a terminal count at which time an indication is given that the filter is becoming blocked aid should be replaced.

The detecting may be made by extraction of information from the output of the detector, or from information derived from a separate detector.

In one form of the invention there is provided a method of producing an indication of blockage of a dust filter in a smoke or fire detection system of the kind having a detector for producing an output indicative of the level of emissions of the products of smoke or fire in air, and the filter being arranged to filter dust from said air before application to the detector, said detector producing in said output an identifiable output signature in the event of detection of a dust particle; the method comprising accumulating a count representing the number of occurrences of said signature up to a terminal count at which time an indication is given that the filter is becoming blocked and should be replaced.

The output signal may represent the magnitude of smoke level in the air and the signature may comprise transient peaks in the output. This is particularly the case where the detector is an optical light scatter detector.

The invention also provides a filter blockage monitoring system for use with a smoke or fire detection system of the kind having a detector for producing an output indicative of the level of emissions of the products of smoke or fire in air, and a filter being arranged to filter dust from said air before application to the detector, said detector producing in said output an identifiable output signature in the event of detection of a dust particle, said system comprising means for identifying occurrences of said output signature and accumulating a count representing the number of those occurrences up to a terminal count at which time an indication is given that the filter is becoming blocked and should be replaced.

The accumulating of the counts may be effected by use of a suitable discriminator device producing an output which adopts a predetermined state when a said output signature is detected and a counter which counts the number of times the predetermined state is assumed.

In another form of the invention there is provided a method of producing an indication of blockage of a dust filter in a smoke or fire detection system of the kind having a detector for producing an output indicative of the level of emissions of the products of smoke or fire in air, and the filter being arranged to filter dust from said air before application to the detector, and a further detector. said further detector being sensitive to presence of dust in said at least part of said air but relatively insensitive to presence of said emissions therein, and producing in the output thereof an identifiable output in the event of detection of a dust particle; the method comprising accumulating a count representing the number of occurrences of said identifiable output up to a terminal count at which time an indication is given that the filter is becoming blocked and should be replaced.

The invention also provides a filter blockage monitoring system for use with a smoke or fire detection system of the kind having a detector for producing an output indicative of the level of emissions of the products of smoke or fire in air, a filter being arranged to filter dust from said air before application to the detector, and a further detector, said further detector being sensitive to presence of dust in said air but relatively insensitive to presence of said emissions therein, said further detector producing an identifiable output in the event of detection of a dust particle, said filter integrity monitoring system comprising means for identifying occurrences of said identifiable output and accumulating a count representing the number of those occurrences up to a terminal count at which time an indication is given that the filter is becoming blocked and should be replaced.

The accumulated count may be reset as appropriate such as when it reaches the predetermined count or when a filter is replaced. Suitable means such as a micro-switch may be provided to enable detection of filter removal for this purpose.

BRIEF DESCRIPTION OF THE DRAWINGS

The invention is described in greater detail hereinafter, by way of example only, with reference to a particular embodiment thereof described herein below and illustrated in the accompanying drawings, wherein.

DETAILED DESCRIPTION

Figure 1:
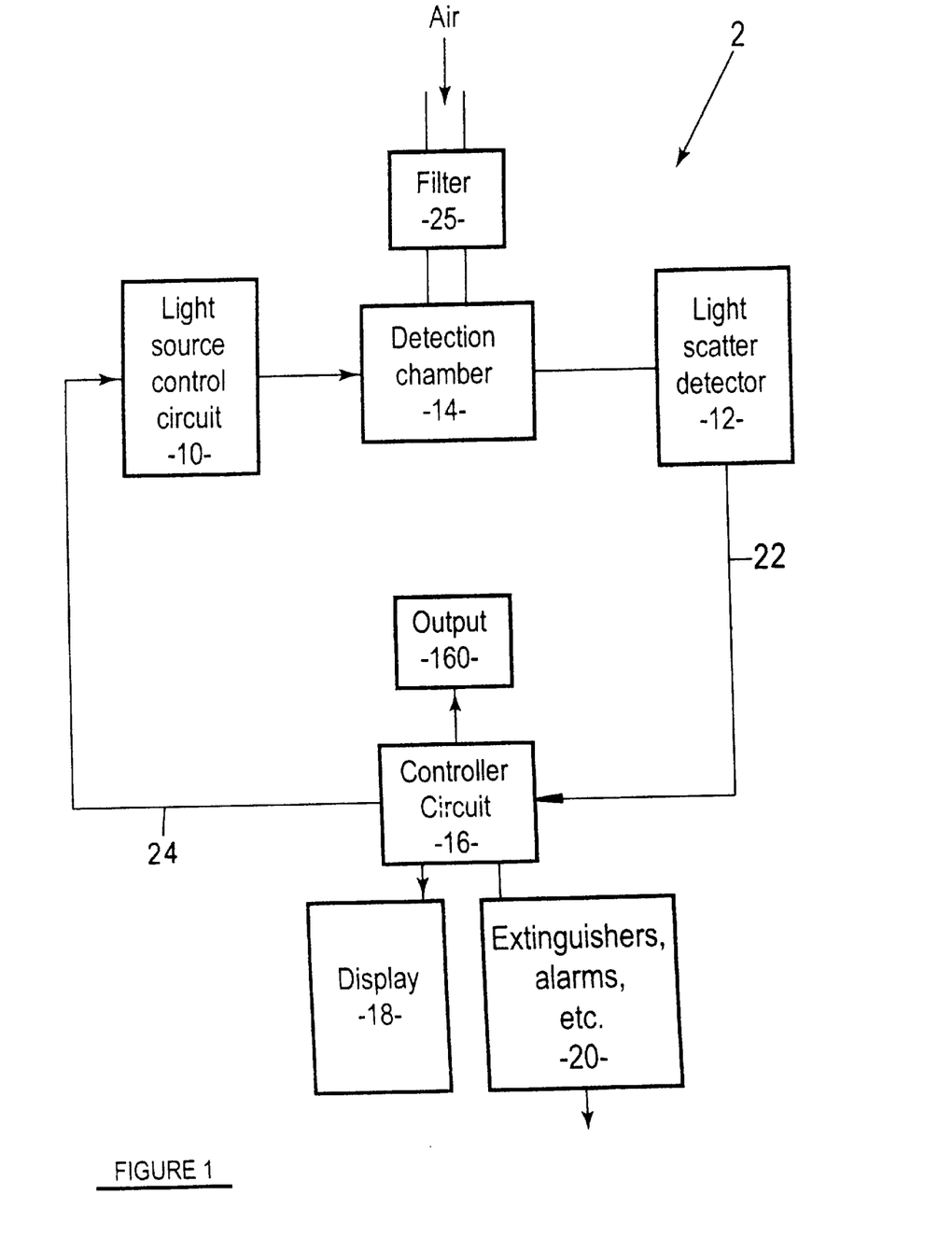
FIG. 1 is a block diagram of an optical scatter detection system, such as in a smoke detector.

An optical scatter detection system 2 is shown in block diagram form in FIG. 1, as utilised in a smoke detector. A light source controlling circuit 10 controls a light source such as a laser light source which illuminates a scatter detection chamber 14. The scatter detection chamber 14 is provided with a source of air in which smoke is to be detected, such as within the building in which the smoke detector is installed. This air is passed into the detector chamber via a suitable filter 25. Light from the light source is scattered by airborne particles introduced into the detection chamber 14, and the scattered light is detected by a light scatter detector 12.

A controller circuit 16 is coupled to the light source controlling circuit 10 and to the light scatter detector 12. Controller circuit 16 receives signal on line 22 from the light scatter detector 12, which signal is indicative of the amount of light reaching the light scatter detector from the laser light source incorporated into the light source control circuit 10, after that light has been scattered by passing through the detection chamber 14. The controller circuit 16 outputs signal on a line 24 to light source controlling circuit 10, to control the light source controlling circuit 10.

The controller circuit 16 may control alarm apparatus, such as a suitable display 18 to indicate the state of the optical scatter detection system, (particularly to indicate risk that fire may be present), based on the light level detected by the detector 12 as compared with the known level of light being generated by the laser light source. Furthermore, the controller circuit 16 may control apparatus such as fire extinguishers, alarms and so on, collectively designated by reference numeral 20 in FIG. 1.

Figure 3:
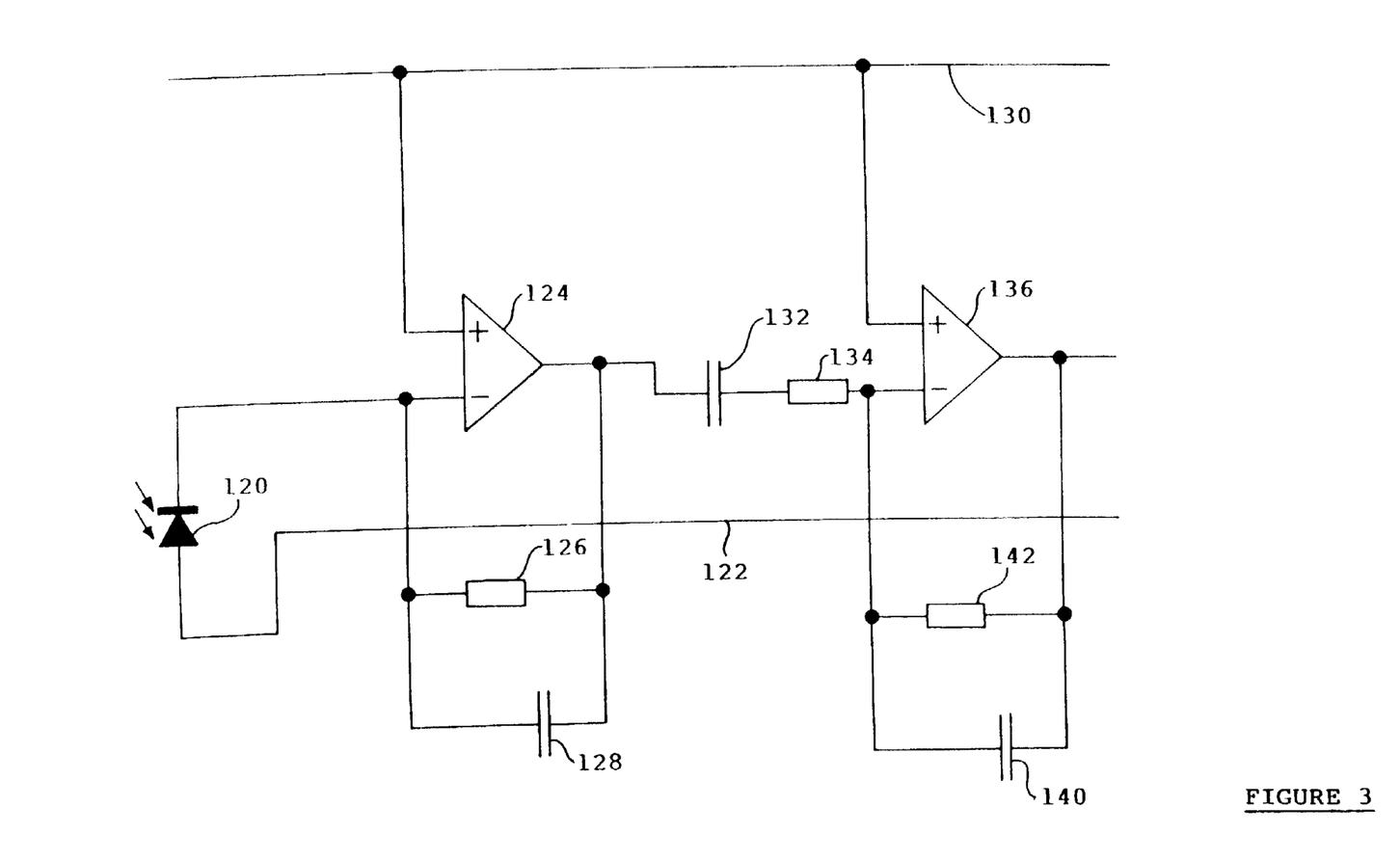
FIG. 3 is a schematic diagram of a light scatter detector incorporated into the system of FIG. 1.

The components of the above system may generally be formed in conventional manner. Detector 12 may be formed as shown in FIG. 3. Here, a photodiode 120 is shown arranged to receive light from the source 10 having passed through the detection chamber 14. Photodiode 120 is between a ground line 122 and the inverting input of an operational amplifier 124. The inverting input and the output of amplifier 124 are connected by the parallel resistor 126 and capacitor 128 shown, and the non-inverting input is connected to voltage bias rail 130.

Output from amplifier 124 is taken via the series connected capacitor 132 and resistor 134 to the inverting input of a second amplifier 136. The non-inverting input of this is again connected to the rail 130, whilst the inverting input and output are connected via the parallel capacitor 140 and resistor 142 shown. The photodiode may for example be of type BPW34 and the operational amplifiers may be of type LMC662. The arrangement of this circuit is such that the first amplifier stage represented by amplifier 124 and associated components generates an output signal proportional to the current from the photodiode 120 and provides a first order low pass filter to remove high frequency noises. The second stage, provided by capacitor 132, resistor 134 and the amplifier 136 and associated components, provides a high pass filter which removes DC offsets and provides additional gain. Output from amplifier 136 is applied to the controller circuit 16, which in the present instance includes the components shown in FIG. 2.

Figure 4:
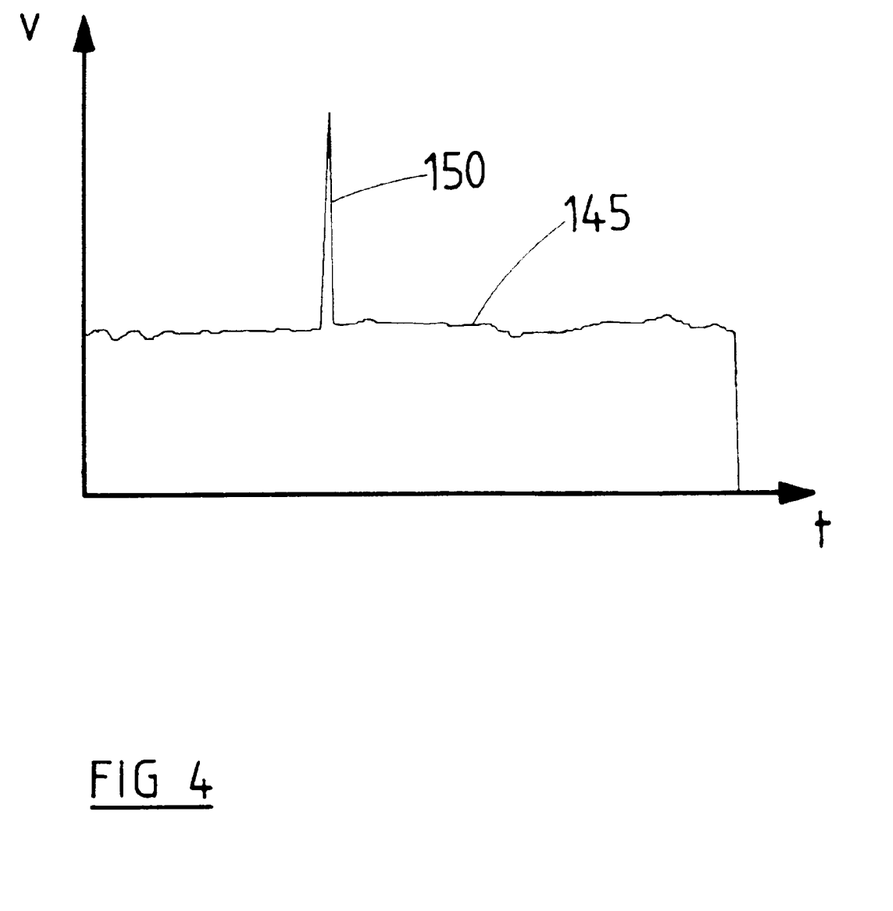
FIG. 4 is a diagram illustrating the output from the detector of FIG. 2.

FIG. 4 shows a representative output signal 145 from the detector 12. In this case, signal 145 is an analog output. The signal level, overall, is representative of the concentration of particles in the air past chamber 14 which are indicative of the presence of smoke or fire. However, when dust particles pass through the filter 25, they produce a characteristic signature in the output as shown. In particular, a spike 150 is produced in the output signal. Generally, there will be one such spike for each detected dust particle. The reason why the dust particles cause spikes of this kind is that the dust particles are much bigger than the particles which are otherwise detected for purposes of smoke or fire detection.

Figure 2:
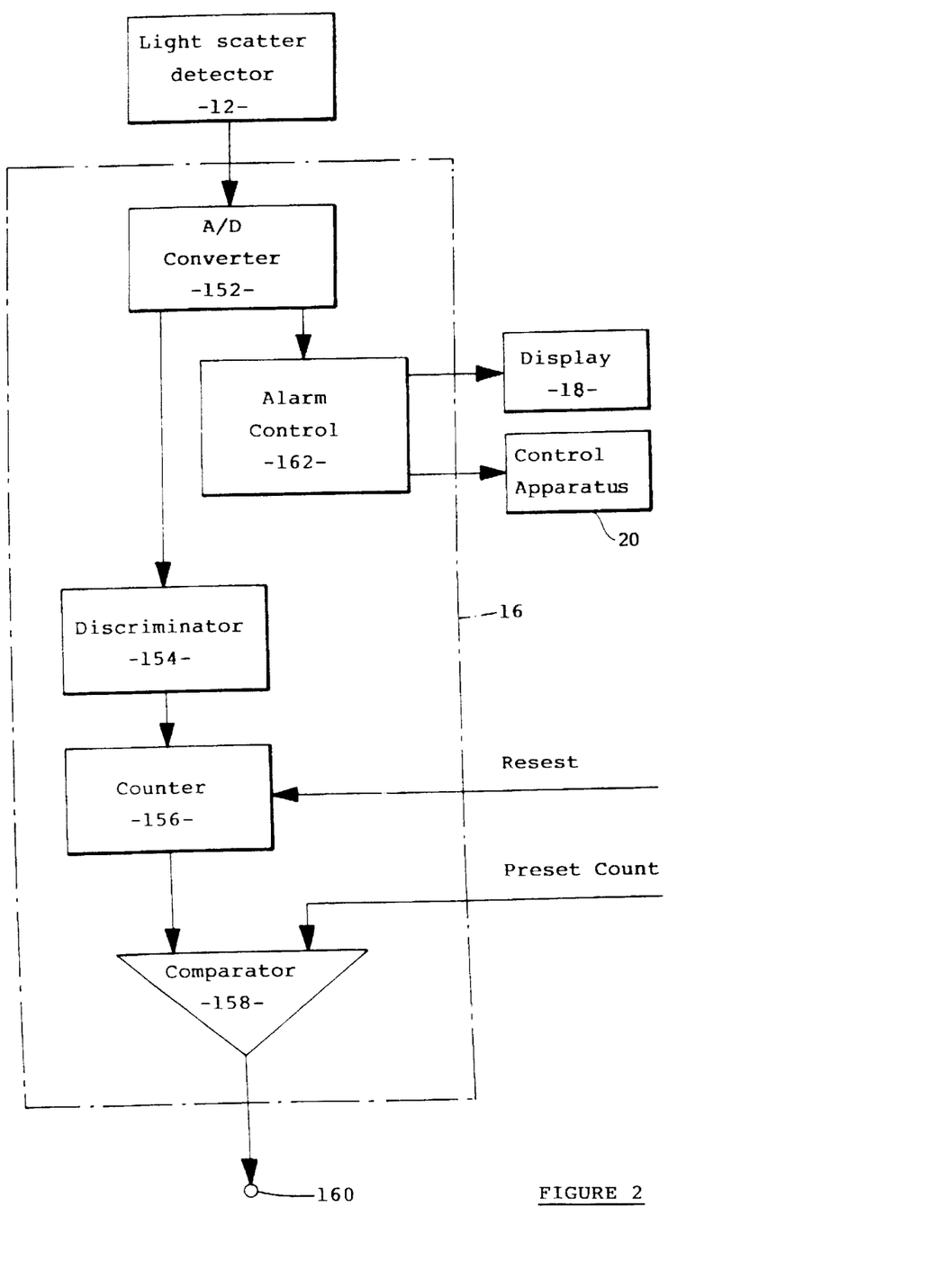
FIG. 2 is a schematic diagram of a controller circuit incorporated into the system of FIG. 1.

In the controller 16, signal of form shown in FIG. 4 is applied to an analog/digital converter 152 to provide a digital signal representative thereof, which digital signal is then applied to a discriminator 154. Discriminator 154 is effective, by computation in accordance with a suitable program of known kind, to distinguish spikes 150 in the signal. At each occurrence of a spike, an output is produced from the discriminator which is applied to a cumulative counter 156. The output from counter 156 is applied to a suitable comparator 158 with a preset count therein and, when the accumulated count from the counter 156 reaches the preset count, an output signal is produced at an output 160 indicative that the filter 25 needs replacement.

The dust count may be arranged to be reset to zero when the filter is new or changed, by resetting counter 156. This re-setting could be done automatically in response to detection of removal of the old filter, or the counter may be reset by an external control device.

For an experimental system, the preset or terminal count was determined to be 10,500,000 for a reduction in smoke flow through the filter of 10%. If a greater reduction in sensitivity is allowable, then a higher terminal count can be used. Where the nature of the filter blockage versus smoke detection sensitivity reduction is not known for any filter type, the terminal counts used may be determined empirically by measuring the reduction in sensitivity until this reaches 10% and noting the dust count.

Studies of dust have failed to agree on what is the normal level of dust, however they have generally agreed that the distribution of dust particle sizes is relatively constant and only the level of dust particles tends to vary widely. It is on this basis it may be assumed that dust will be predictable in its particle size distribution and only the level will vary. A volume filter is a statistical device with the probability of a particle getting through going up as the particle size reduces. This means that the output of the filter will contain very few large particles, more medium sized particle and many small particles with gases going through with very little absorption in the filter. For example, one type of open cell foam filter used exhibited a 3% chance of a 20 micron particle passing through.

Because the distribution of particle sizes remains relatively constant and the filter is a statistical device, it is possible to infer the input to the filter from the output. The number of dust particles that get through the filter will be a fixed fraction of the number that went into the filter and, therefore constitute a good indicator of how dusty the environment is.

As a volume filter fills up, its characteristics change and less dust gets through. After a while very small particles such as smoke begin to become tapped in the filter and smoke detector sensitivity goes down. By empirically determining when this will happen it is possible to indicate when a filter needs to be changed and prevent early replacement of good filters and also prevent loss of smoke detector sensitivity due to the filter starting to fill with dust. Since the output of dust from the filter is indicative of the dust input to the filter the filter can be effectively monitored by counting the dust output from the filter .and a terminal count can be used to determine when a filter should be changed.

The functions above described, carried out in relation to assessing filter integrity, may be separately effected in controller circuit 16, from functions associated with extraction of alarm signals based on signal from detector 12, or may be effected as part of general signal processing in controller circuit 16. In the arrangement, shown the generation of alarm signals is separately effected by the circuit 162 shown.

Figure 5:
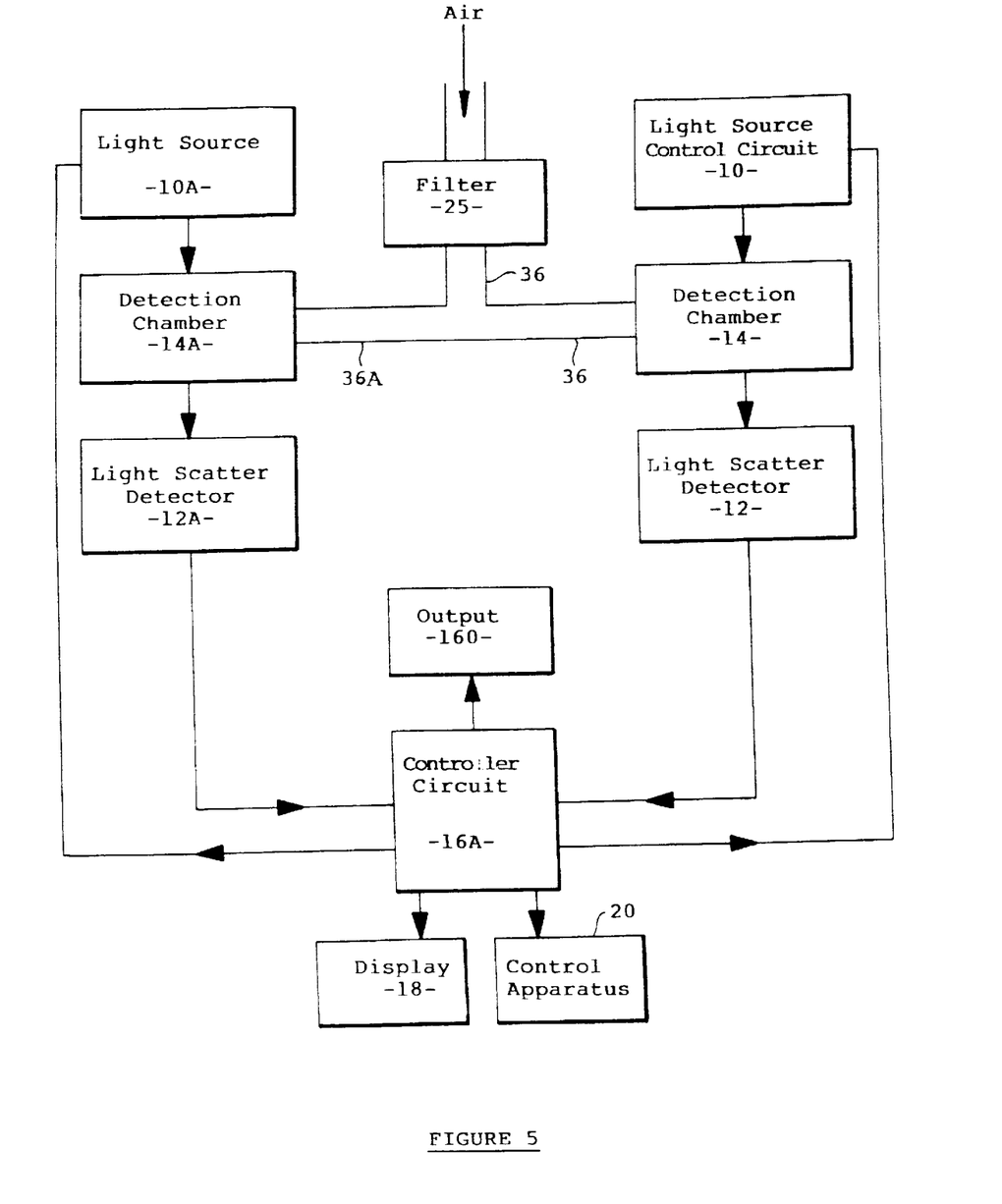
FIG. 5 is a block diagram of a further optical scatter detection system formed in accordance with the invention, such as in a smoke detector.
Figure 6:
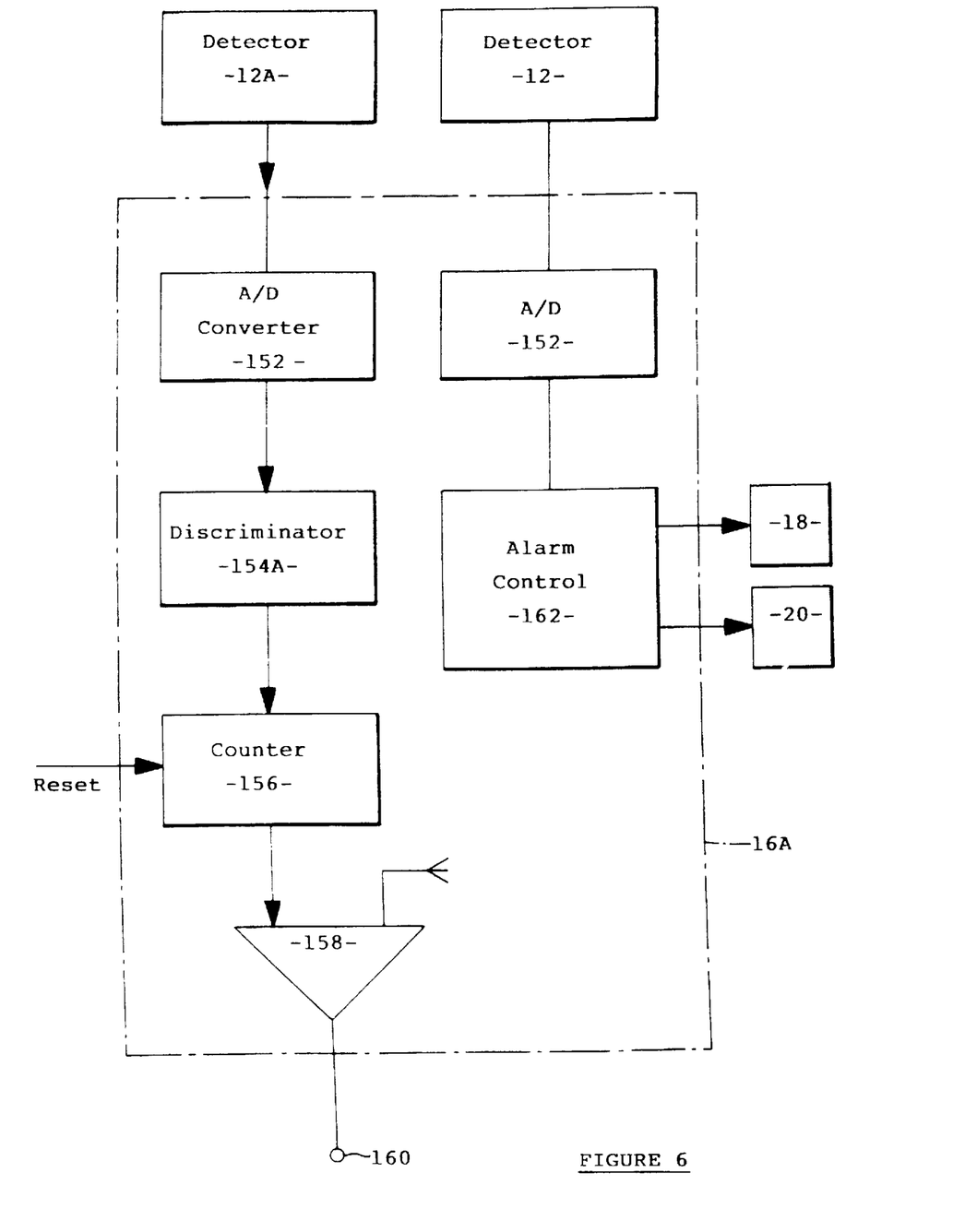
FIG. 6 is a schematic diagram of a controller circuit incorporated into the system of FIG. 5.

The described form of the invention utilises a discriminator 154 which is able to discriminate, in the output produced by light scatter detector 12, signal characteristics which are indicative of detection of dust particles from signal characteristics which are associated with detection of emissions to do with fire or smoke detection. It is not, however, essential that the invention be practised in this fashion. FIG. 5 and FIG. 6 show a modified arrangement in which a simpler form of processing may be effected. The arrangement of FIGS. 5 and 6 utilises a detection chamber 14, light source control circuit 10 and light scatter detector 12 of similar construction to those which may be employed in the arrangement of FIG. 1 Likewise, air may be passed to the chamber 14 via a duct 36 and through the described filter 25. In this case, the controller circuit 16A is somewhat similar to controller circuit 16 and, as shown in FIG. 6, includes an analog digital converter 152 and an alarm control circuit 162 which is effective to control items such as the described display 18 and extinguisher alarms 20.

In the arrangement of FIGS. 5 and 6, however, there is provided an additional light source control circuit 10A, detection chamber 14A and light scatter detector 12A. These may be somewhat similar to the control circuit 10, detection chamber 14 and detector 12, but the detector 12A is arranged so as to be relatively insensitive to presence of small particles characteristic of emissions from smoke or fire but relatively sensitive to larger dust particles.

The chamber 14A is connected to a branch duct 36A from duct 36 so that a part of the air introduced to duct 36 after having passed through filter 25 is passed to chamber 14A. Thus, the output from the detector 12A is in this case representative substantially only of the presence of dust particles. Thus, a characteristic peak associated with each dust particle as it is detected will be generated at the output from this detector.

Within controller circuit 16A, the analog output from detector 12A is passed to an analog to digital converter 152 and then to a discriminator 154A which in this case does not have to perform manipulation of the signal applied thereto, but merely to provide a characteristic signal each time the characteristic signal corresponding to the detection of a dust particle arises. The latter signal may, for example, be a simple pulse arising each time a peak in the analog signal applied to converter 152 arrives from the detector 12A. Thus, counter 156 can count occurrences of this characteristic signal to produce the required count of the number of dust particles, and may be arranged to provide an output to the comparator 158 in the same fashion as previously described. Thus, there is again produced at output 160, when the count from counter 156 reaches the predetermined count applied to comparator 158, a signal indicating that the filter integrity has dropped below a predetermined value.

The arrangement shown in FIGS. 5 and 6 may require more components than the arrangement in FIG. 1, but on the other hand the signal manipulation required to be done by the controller circuit 16A is less than in the case of controller 16 forming the arrangement of FIG. 1.

The system of FIGS. 5 and 6 may be further modified so that the air delivered to chamber 14A is derived directly from the incoming air to filter 25 rather than the outlet air from the filter. In this case, a higher terminal count will be required because there will be more dust present. Particularly in this case, branch duct 36A could be omitted, with air input to the detection chamber 14A being directed from the surrounding air before passing through the filter 25.

The described construction has been advanced merely by way of explanation, and many modifications and variations may be made thereto without departing from the spirit and scope of the invention as defined by the appended claims.

I claim:

1. A method of producing an indication of blockage of a dust filter in a smoke or fire detection system of the kind having a detector for producing an output indicative of the level of emissions of the products of smoke or fire in air, and the filter being arranged to filter dust from said air before application to the detector, comprising detecting dust particles in said air either before or after passage through said filter and making a cumulative count over time of the number of so detected dust particles up to a terminal count at which time an indication is given that the filter is becoming blocked and should be replaced.

2. A method as claimed in claim 1 wherein said detecting is made by extraction of information from the output of the detector.

3. A method as claimed in claim 1 wherein said detecting is made from information derived from a separate detector.

4. A filter blockage monitoring system for use with a smoke or fire detection system of the kind having a detector for producing an output indicative of the level of emissions of the products of smoke or fire in airs and a filter being arranged to filter dust from said air before application to the detector, said detector producing in said output an identifiable output in the event of detection of a dust particle, said filter blockage monitoring system comprising means for detecting dust particles in said air either before or after passage through said filter and making a cumulative count over time of the number of so detected dust particles up to a terminal count at which time an indication is given that the filter is becoming blocked and should be replaced.

5. A filter blockage monitoring system as claimed in claim 4 wherein said means for detecting effects said detecting by extraction of information from the output of the detector.

6. A filter blockage monitoring system as claimed in claim 4 wherein said means for detecting effects said detecting from information derived from a separate detector.

7. A method of producing an indication of blockade of a dust filter in a smoke or fire detection system of the kind having a detector for producing an output indicative of the level of emissions of the products of smoke or fire in air, and the filter being arranged to filter dust from said air before application to the detector, said detector producing in said output an identifiable output signature in the event of detection of a dust particle; the method comprising accumulating a count representing the number of occurrences of said signature up to a terminal count at which time an indication is given that the filter is becoming blocked and should be replaced.

8. A method as claimed in claim 7 wherein the output signal represents the magnitude of smoke level in the air and the signature comprises transient peaks in the output.

9. A method as claimed in claim 7 wherein the detector is an optical light scatter detector.

10. A filter blockage monitoring system for use with a smoke or fire detection system of the kind having a detector for producing an output indicative of the level of emissions of the products of smoke or fire in air, and a filter being arranged to filter dust from said air before application to the detector, said detector producing in said output an identifiable output signature in the event of detection of a dust particle, said system comprising means for identifying occurrences of said output signature and accumulating a count representing the number of those occurrences up to a terminal count at which time an indication is given that the filter is becoming blocked and should be replaced.

11. A filter blockage monitoring system as claimed in claim 10 wherein the means for identifying includes a discriminator device effective for effecting said accumulating, said discriminator device producing an output which adopts a predetermined state when a said output signature is detected, and having a counter which counts the number of times the predetermined stile is assumed.

12. A method of producing an indication of blockage of a dust filter in a smoke or fire detection system of the kind having a detector for producing an output indicative of the level of emissions of the products of smoke or fire in air, and the filter being arranged to filter dust from said air before application to the detector, and a further detector, said further detector being sensitive to presence of dust in said at least part of said air but relatively insensitive to presence of said emissions therein, and producing in the output thereof an identifiable output in the event of detection of a dust particle; the method comprising accumulating a count representing the number of occurrences of said identifiable output up to a terminal count at which time an indication is given that the filter is becoming blocked and should be replaced.

13. A method as claimed in claim 12 wherein the air to which the further detector is exposed comprises air before passage through the filter.

14. As method as claimed in claim 12 wherein the air to which the further detector is exposed comprises air after passage through the filter.

15. A method as claimed in claim 12 wherein the accumulated count is reset when it reaches a predetermined count or when a filter is replaced.

16. A method as claimed in claim 12 wherein means is provided to enable detection of filter removal.

17. A filter blockage monitoring system for use with a smoke or fire detection system of the kind having a detector for producing an output indicative of the level of emissions of the products of smoke or fire in air, a filter being arranged to filter dust from said air before application to the detector, and a further detector, said further detector being sensitive to presence of dust in said air but relatively insensitive to presence of said emissions therein, said further detector producing an identifiable output in the event of detection of a dust particle, said filter integrity monitoring system comprising means for identifying occurrences of said identifiable output aid accumulating a count representing the number of those occurrences up to a terminal count at which time an indication is given that the filter is becoming blocked and should be replaced.

18. A method as claimed in claim 17 wherein the air to which the further detector is exposed comprises air before passage through the filter.

19. As method as claimed in claim 18 wherein the air to which the further detector is exposed comprises air after passage through the filter.

* * * * *